United States Patent [19]
Ohnishi et al.

[11] Patent Number: 5,824,449
[45] Date of Patent: Oct. 20, 1998

[54] PROCESS FOR PRODUCING D-MALIC ACID

[75] Inventors: Norimasa Ohnishi, Kawasaki; Chisa Niwa, Saga-ken; Kenzo Yokozeki, Kawasaki, all of Japan

[73] Assignee: Ajinomoto Co., Inc., Tokyo, Japan

[21] Appl. No.: 840,448

[22] Filed: Apr. 18, 1997

[30] Foreign Application Priority Data

Apr. 19, 1996 [JP] Japan ..................................... 8-098110

[51] Int. Cl.⁶ ...................................................... C12P 7/46
[52] U.S. Cl. .......................... 435/145; 435/822; 435/847; 435/901; 435/911
[58] Field of Search .................................... 435/145, 847, 435/822, 909, 911

[56] References Cited

U.S. PATENT DOCUMENTS 4,912,042  3/1990  Laumen ................................... 435/145
5,270,190  12/1993 Nakayama et al. ..................... 435/145

*Primary Examiner*—Herbert J. Lilling
*Attorney, Agent, or Firm*—Oblon, Spivak, McClelland, Maier & Neustadt, P.C.

[57] ABSTRACT

A process for producing D-malic acid selectively without producing L-malic acid, using inexpensive maleic acid as a starting material, may be carried out using a microorganism belonging to the genus Erwinia, Mycoplana, Sporosarcina, Vibrio, Geotrichum or Torulaspora. The microorganism may be separated from the culture, used as a culture, or a treated microorganism.

20 Claims, No Drawings

PROCESS FOR PRODUCING D-MALIC ACID

BACKGROUND OF THE INVENTION

1. Field of the Invention

The present invention relates to a process for producing D-malic acid. D-malic acid is useful as a starting material for the synthesis of a wide variety of pharmaceutical and chemical compounds.

2. Description of the Background

Conventionally known methods of producing D-malic acid include chemical synthesis (A. Bernard et al., Tetrahedron, Vol. 46, pp. 1987–1998 (1990)); several reaction steps are required and optical purity of the malic acid is low. Optical resolution of racemic malic acid after conversion into a diastereomeric salt is also known (Japanese Patent LOP Publication Nos. 56439/1982 and 204741/1985), but is not considered economical because an expensive resolution agent such as quinine, etc., is required. Another known method uses a microorganism to act on racemic malic acid, assimilating only the L-malic acid, and then recovering the remaining D-malic acid (Japanese Patent LOP Publication No. 242699/1990). A disadvantage of this method is that the maximum molar yield from the racemic mixture is 50%, and the optical purity of D-malic acid produced is low.

On the other hand, a method of forming D-malic acid directly from maleic acid using microorganisms is also known (J. Mariet et al., Appl. Environ. Microbiol., Vol. 58, pp. 2854–2960 (1992), Japanese Patent LOP Publication Nos. 316491/1992, 188/1995, and 143891/1995). However, all these prior methods suffer from a variety of disadvantages: the optical purity of the D-malic acid formed is low; expensive inducers must be added to the culture medium; and large amounts of microorganisms must be used in the reaction, because of the low rate of formation of D-malic acid. There is a report that microorganisms of the genus Arthrobacter can be used to produce D-malic acid from maleic acid (Japanese Patent LOP Publication No. 103680/1993). According to this report, the optical purity of the D-malic acid formed is high and the production yield is also high. In this method, however, the microorganisms having high activity are limited to those of the genus Arthrobacter, and no other microorganisms having the ability to effectively produce D-malic acid have been found.

SUMMARY OF THE INVENTION

An object of the present invention is to provide a process for producing D-malic acid inexpensively and easily.

The present inventors have found microorganisms capable of efficiently producing D-malic acid with extremely high optical purity from maleic acid.

The present invention provides a process for producing D-malic acid, in which a culture of a microorganism belonging to the genus Erwinia, Mycoplana, Sporosarcina, Vibrio, Geotrichum or Torulaspora and having the ability to produce D-malic acid from maleic acid, or the microorganism itself separated from the culture, or a treatment microorganism obtained from the said microorganisms, is allowed to act on maleic acid in order to form D-malic acid.

DETAILED DESCRIPTION OF THE INVENTION

The microorganism used in the present invention may be any microorganisms which belong to the genera Erwinia, Mycoplana, Sporosarcina, Vibrio, Geotrichum and Torulaspora and which have the ability to produce D-malic acid from maleic acid. Examples of specific strains are *Erwinia amylovora* IFO 12687, *Mycoplana dimorpha* ATCC 4279, *Sporosarcina ureae* IFO 12698, *Vibrio tyrogene* AJ 2807 (FERM BP-5848) which was deposited at NIBH (National Institute of Bioscience and Human Technology) on Mar. 4, 1997, *Geotrichum fragrans* CBS 152.25, and *Torulaspora delbrueckii* IFO 1083.

The microorganisms of the present invention may be cultured in any medium which the microorganism can be grown. For example, a conventional liquid nutrient medium containing a carbon source, a nitrogen source, inorganic salts, organic nutrients, etc., may be used.

The carbon source is any which can be used by the microorganism. Examples include sugars such as glucose, fructose, sucrose, dextrin, etc.; alcohols such as sorbitol, ethanol, glycerol, etc.; organic acids such as fumaric acid, citric acid, acetic acid, propionic acid, etc.; or salts thereof, or mixtures thereof.

The nitrogen sources which may be used include e.g. inorganic ammonium salts, such as ammonium sulfate, ammonium chloride, etc.; organic ammonium salts, such as ammonium fumarate, ammonium citrate, etc.; nitrates such as sodium nitrate, potassium nitrate, etc.; organic nitrogen compounds, such as peptone, yeast extract, meat extract, corn steep liquor, etc.; or mixture thereof.

Further, a conventionally used nutrient source, such as inorganic salts, trace metal salts, vitamins, etc. may be mixed with the medium. If necessary, it is also possible to add a growth promoter for the microorganism; an enhancer, such as maleic acid, etc. for raising the ability to form the target compound of the present invention; or a substance effective for maintaining medium pH.

The microorganisms are cultured under conditions suitable for their growth at a pH of 4 to 9, preferably 6 to 8, at a temperature of 20° to 45° C., preferably 25° to 37° period of 5 to 72 hours, preferably 12 to 48 hours or thereabout.

To allow the microorganisms to act on maleic acid, maleic acid may be added to the culture thus obtained; alternatively, the microorganisms may be separated from the culture by centrifugation, etc., then optionally washed, and suspended again in a buffer, water, etc., and then maleic acid may be added to this suspension.

Treated microorganism, prepared from the microorganisms, may be used. Treated microorganisms include disrupted microorganisms, microorganisms treated with acetone, lyophilized microorganisms, or microorganisms immobilized by conventional methods using polyacrylamide gel, carrageenan, alginate gel, etc. As treated microorganisms, it is also possible to employ an extract of the microorganisms; or the enzymes catalyzing the reaction which have been separated and purified from the extract.

Solid maleic acid, or a solution of maleic acid in water or in a buffer, may be added at the start of the reaction or in portions during reaction. Though not particularly limited, the concentration of maleic acid added is preferably about 0.1 to 10% (weight/volume%).

The reaction may be promoted by adding surface active agents, such as Triton X-100, Triton N-101, Tween 20, Tween 60, etc. to the reaction mixture.

The reaction may be carried out at a pH of 6 to 9, preferably 6.5 to 8.0, at a temperature of 10° to 60° C., preferably 30 to 45° C., with or without shaking. After the 1 to 120 hours under these reaction conditions, a significant amount of D-malic acid forms and accumulates in the reaction mixture.

Using conventional purification methods such as salting-out, column chromatography, etc., the D-malic acid formed by the reaction may be easily recovered from the reaction solution directly, or after removal of the microorganisms.

The microorganism may be a biologically pure preparation, such as isolated from other types of microorganisms, or purified.

EXAMPLES

Hereinafter, the present invention is described in more detail by reference to Examples. In Examples, the optical activity and reaction yield of D-malic acid were determined by high performance liquid chromatography under the following conditions:

Column: SUMICHIRAL OA-5000 (available from Sumitomo Bunseki Center K.K.)

Eluent: 1 mM copper acetate plus 0.1 M aqueous ammonium acetate/isopropanol (85/15).

Flow rate: 1.0 ml/min.

Detection: UV 254 nm.

Retention time: D-malic acid, 7.4 minutes; L-malic acid, 1.8 minutes.

Example 1

A medium (pH 7.0) composed of 1.0% glycerol, 0.2% maleic acid, 0.5% $(NH_4)_2SO_4$, 0.3% $K_2PO_4$, 0.05% $MgSO_4 \cdot 7H_2O$, 0.001% $FeSO_4 \cdot 7H_2O$, 0.001% $MnSO_4 \cdot 4H_2O$, 1.0% yeast extract and 1.0% polypeptone was pipetted into 500-ml flasks in an amount of 50 ml medium per flask, and sterilized by autoclaving at 120° C. for 15 minutes (the unit "%" above is weight/volume %). Each of *Erwinia amylovora* IFO 12687, *Mycoplana dimorpha* ATCC 4279, *Sporosarcina ureae* IFO 12698 and *Vibrio tyrogenes* FERM BP-5848, previously cultured in a bouillon agar medium at 30° C. for 24 hours, was inoculated via a platinum needle into each flask of the above medium, and cultured at 30° C. for 24 hours under shaking. After cultivation, the microorganisms were separated from the broth by centrifugation, then washed with 100 mM phosphate buffer (pH 7.0) in the same volume as the culture, and suspended in 100 mM phosphate buffer with the same weight as the resulting wet microorganisms. To 1 ml of this microbial suspension was added 9 ml of the same buffer containing 200 mg maleic acid and 100 mg Triton X-100, and further reaction was carried out at 30° C. for 20 hours. A part was then taken from each reaction mixture and examined for the amount of D-malic acid and L-malic acid formed. The results are shown in Table 1. Every strain produced D-malic acid well, but no L-malic acid was formed.

TABLE 1

| Strains | Malic Acid Formed (mg/ml) | |
|---|---|---|
| | D-isomer | L-isomer |
| *Erwinia amylovora* IFO 12687 | 7.5 | 0 |
| *Mycoplana dimorpha* ATCC 4279 | 11.0 | 0 |
| *Sporosarcina ureae* IFO 12698 | 16.4 | 0 |
| *Vibrio tyrogenes* FERM BP-5848 | 7.2 | 0 |

Example 2

A medium (pH 6.0) composed of 1.0% glycerol, 0.2% maleic acid, 0.5% $(NH_4)_2SO_4$, 0.3% $K_2HPO_4$, 0.1% $KH_2PO_4$, 0.005% $MgSO_4 \cdot 7H_2O$, 0.001% $FeSO_4 \cdot 7H_2O$, 0.001% $MnSO_4 \cdot 4H_2O$, 0.5% yeast extract, 1.0% polypeptone and 0.5% malt extract was pipetted into 500-ml flasks, in an amount of 50 ml medium per flask, and sterilized by autoclaving at 120° C. for 15 minutes (the unit "%" above is weight/volume %). Each of *Geotrichum fragrans* CBS 152.25 and *Torulaspora delbrueckii* IFO 1083, previously cultured at 30° C. for 48 hours in a potato dextrose agar medium, was inoculated via a platinum needle into each flask of the above medium, and cultured at 30° C. for 24 hours under shaking. After cultivation, the microorganisms were separated from the culture by centrifugation, then washed with 100 mM phosphate buffer (pH 7.0) in the same volume as the culture, and suspended in 100 mM phosphate buffer with the same weight as the resulting wet microorganisms. 0.5 g of glass beads of 0.4 mm in diameter were added to 1 ml of the microbial suspension and the microorganisms were disrupted for 20 minutes with a minibead beater (Biospec Co., Ltd.). To the whole of the resulting suspension of disrupted microorganisms was added 9 ml of the same buffer containing 200 mg maleic acid and 100 mg of Triton X-100, and further reaction was carried out at 30° C. for 20 hours. A part was then taken from each reaction solution and examined for the amount of D-malic acid and L-malic acid formed. The results are shown in Table 2. Both of the strains produced D-malic acid well, but no L-malic acid was formed.

TABLE 2

| Strains | Malic Acid Formed (mg/ml) | |
|---|---|---|
| | D-isomer | L-isomer |
| *Geotrichum fragrans* CBS 152.25 | 3.7 | 0 |
| *Torulaspora delbrueckii* IFO 1083 | 4.8 | 0 |

Obviously, additional modifications and variations of the present invention are possible in light of the above teachings. It is therefore to be understood that within the scope of the appended claims, the invention may be practiced otherwise than as specifically described herein.

The priority document of the present application, Japanese Patent Application No. 098110/1996, filed on Apr. 19, 1996, is hereby incorporated by reference.

What is claimed as new and is desired to be secured by Letters Patent of the United States is:

1. A process for producing D-malic acid, comprising:
   contacting a mixture with a microorganism or a treated form of said microorganism,
   wherein said microorganism is selected from the genera consisting of Erwinia, Mycoplana, Sporosarcina, Vibrio, Geotrichum, Torulaspora, and mixtures thereof, and
   said mixture comprises maleic acid.

2. The process of claim 1, wherein said microorganism is selected from the species consisting of *Erwinia amylovora, Mycoplana dimorpha, Sporosarcina ureae, Vibrio tyrogenes, Geotrichum fragrans, Torulaspora delbrueckii,* and mixtures thereof.

3. The process of claim 1, wherein said microorganism is selected from the strains consisting of *Erwinia amylovora* IFO 12687, *Mycoplana dimorpha* ATCC 4279, *Sporosarcina ureae* IFO 12698, *Vibrio tyrogenes* AJ2807 (FERM BP-5848), *Geotrichum fragrans* CBS 152.25, *Torulaspora delbrueckii* IFO 1083, and mixtures thereof.

4. The process of claim 1, wherein said mixture further comprises a surfactant.

5. The process of claim 1, wherein said mixture further comprises a buffer.

6. The process of claim 1, wherein said mixture consists essentially of said maleic acid.

7. The process of claim 6, wherein said mixture further consists essentially of a surfactant, optionally a buffer, and optionally D-malic acid.

8. The process of claim 1, wherein said mixture consists of:

(a) maleic acid, (b) a microorganism, a treated form of said microorganism, or a mixture of said microorganism and a treated form of said microorganism, (c) water, (d) optionally at least one surfactant, (e) optionally at least one buffer, and (f) optionally D-malic acid.

9. The process of claim 3, wherein said mixture further comprises a surfactant.

10. The process of claim 3, wherein said mixture further comprises a buffer.

11. The process of claim 3, wherein said mixture consists essentially of said maleic acid.

12. The process of claim 1, wherein said microorganism or said treated form of said microorganism is an enzyme which catalyzes the reaction of maleic acid to D-malic acid.

13. The process of claim 1, further comprising culturing said microorganism in a medium.

14. The process of claim 1, wherein said contacting is carried out at a temperature of 10°–60° C., and a pH of 6 to 9.

15. The process of claim 1, wherein said maleic acid is present in an amount of 0.1–10 weight/volume %.

16. The process of claim 1, further comprising isolating D-malic acid produced during said contacting.

17. A mixture comprising maleic acid, and a microorganism or a treated from of said microorganism, wherein said microorganism is selected from the genera consisting of Erwinia, Mycoplana, Sporosarcina, Vibrio, Geotrichum, Torulaspora, and mixtures thereof.

18. The mixture of claim 17, wherein said microorganism is selected from the strains consisting of *Erwinia amylovora* IFO 12687, *Mycoplana dimorpha* ATCC 4279, *Sporosarcina ureae* IFO 12698, *Vibrio tyrogenes* AJ2807 (FERM BP-5848), *Geotrichum fragrans* CBS 152.25, *Torulaspora delbrueckii* IFO 1083, and mixtures thereof.

19. A mixture comprising

D-malic acid, and a microorganism or a treated from of said microorganism, wherein said microorganism is selected from the genera consisting of Erwinia, Mycoplana, Sporosarcina, Vibrio, Geotrichum, Torulaspora, and mixtures thereof.

20. The mixture of claim 19, wherein said microorganism is selected from the strains consisting of *Erwinia amylovora* IFO 12687, *Mycoplana dimorpha* ATCC 4279, *Sporosarcina ureae* IFO 12698, *Vibrio tyrogenes* AJ2807 (FERM BP-5848), *Geotrichum fragrans* CBS 152.25, *Torulaspora delbrueckii* IFO 1083, and mixtures thereof.

* * * * *